(12) United States Patent
Martinez et al.

(10) Patent No.: US 12,070,315 B2
(45) Date of Patent: Aug. 27, 2024

(54) EPIDERMAL PAPER-BASED ELECTRONIC DEVICES

(71) Applicant: Purdue Research Foundation, West Lafayette, IN (US)

(72) Inventors: Ramses Valentin Martinez, West Lafayette, IN (US); Behnam Sadri, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 475 days.

(21) Appl. No.: 16/842,953

(22) Filed: Apr. 8, 2020

(65) Prior Publication Data

US 2020/0333829 A1 Oct. 22, 2020

Related U.S. Application Data

(60) Provisional application No. 62/836,098, filed on Apr. 19, 2019.

(51) Int. Cl.
| | |
|---|---|
| A61B 5/257 | (2021.01) |
| A61B 5/00 | (2006.01) |
| A61B 5/263 | (2021.01) |
| A61F 7/00 | (2006.01) |
| D21H 21/16 | (2006.01) |

(Continued)

(52) U.S. Cl.
CPC ............. *A61B 5/257* (2021.01); *A61B 5/263* (2021.01); *A61B 5/68335* (2017.08); *A61F 7/007* (2013.01); *D21H 21/16* (2013.01); *D21H 21/20* (2013.01); *A61F 2007/0052* (2013.01); *A61F 2007/126* (2013.01)

(58) Field of Classification Search
CPC ..... A61B 5/291; A61B 5/68335; A61B 5/263; A61B 5/257; A61F 7/007; A61F 2007/0052; A61F 2007/126; D21H 21/16; D21H 21/20
See application file for complete search history.

(56) References Cited

U.S. PATENT DOCUMENTS

2010/0234716 A1* 9/2010 Engel .................... A61B 5/6833
600/459
2017/0325724 A1* 11/2017 Wang ................... A61B 5/1486

FOREIGN PATENT DOCUMENTS

| WO | WO-2014149465 A1 * | 9/2014 | ............. D21H 27/00 |
| WO | WO-2017181027 A1 * | 10/2017 | ........ A61M 37/0015 |
| WO | WO-2018094409 A1 * | 5/2018 | ........... A61B 5/1477 |

OTHER PUBLICATIONS

Glavan A. et al., Omniphobic "RF Paper" Produced by Silanization of Paper with Fluoroalkyltrichlorosilanes. Adv. Funct. Mater. 2014, 24, 60-70.

(Continued)

*Primary Examiner* — Carl H Layno
*Assistant Examiner* — Aya Ziad Bakkar
(74) *Attorney, Agent, or Firm* — Purdue Research Foundation

(57) ABSTRACT

The present disclosure relates to a novel epidermal paper-based electronic devices (EPEDs), and the methods of making and using the epidermal paper-based electronic devices. The epidermal paper-based electronic devices comprise an electrically conductive layer; and a paper layer with a first hydrophilic side and a second omniphobic side, wherein the electrically conductive layer is attached to the first hydrophilic side of the paper layer.

4 Claims, 7 Drawing Sheets

(51) Int. Cl.
*D21H 21/20* (2006.01)
*A61F 7/12* (2006.01)

(56) References Cited

OTHER PUBLICATIONS

Pal A. et al., Early detection and monitoring of chronic wounds using low-cost, omniphobic paper-based smart bandages. vol. 117, Oct. 15, 2018, pp. 696-705.

* cited by examiner

EPIDERMAL PAPER-BASED ELECTRONIC DEVICES

CROSS-REFERENCE TO RELATED APPLICATION

This patent application claims the priority benefit of U.S. Provisional Application No. 62/836,098, filed Apr. 19, 2019, the content of which is hereby incorporated by reference in its entirety.

TECHNICAL FIELD

The present disclosure relates to a novel epidermal paper-based electronic devices (EPEDs), and the methods of making and using the epidermal paper-based electronic devices.

BACKGROUND

This section introduces aspects that may help facilitate a better understanding of the disclosure. Accordingly, these statements are to be read in this light and are not to be understood as admissions about what is or is not prior art.

The recent development of stretchable, epidermal electronic systems (EES) has demonstrated exciting practical applications in continuous health monitoring, prosthetics, implantable devices, and advanced robotics. Examples of these skin-mountable electronics range from highly conformal sensors for pressure, strain, temperature, and electrophysiological signals, to actuators for optogenetic stimulation, localized heat therapy, or the controlled release of healing factors. The high electrical stability upon bending, twisting, and stretching of EES relies on their conductive electrodes, commonly fabricated by patterning thin layers of ductile metals into serpentine paths, fractal geometries, or self-similar designs, to avoid mechanical impedance mismatch with soft biological tissues. Stretchable thin-film electrodes are, however, easily damaged due to accidental over-stretching beyond their fracture limit, the propagation of defect-induced cracks, or delamination. Several non-conventional methods to fabricate stretchable electrodes using nanocomposites comprising percolating nanoparticles, conducting nanowires or nanomeshes, and microfluidic channels filled with ultralow modulus conductive materials have been proposed to enhance the mechanical performance of skin-mountable devices and to provide them with self-healing properties, and improved resistance to scratches and fatigue. These non-conventional fabrication strategies, however, often require additional layers to encapsulate the nanocomposite, increasing the volume of the final device. Moreover, fabrication techniques typically used to generate skin-mountable electronics often involve high capital equipment and operating costs, hazardous chemicals, and several processing steps. This increases the complexity of the fabrication process and the final cost of the devices, greatly limiting their practical utilization, especially for single-use medical applications.

A rapid, simple, and scalable process to fabricate disposable, mechanically reinforced EES at a low cost, would be desirable to accelerate the development and commercialization of wearable and implantable biomonitoring sensors and actuators, as well as to promote their adoption in clinical settings, especially in resource-limited areas.

Therefore, a rapid, simple, and scalable process to fabricate disposable, mechanically reinforced EES at a low cost would be desirable to accelerate the development and commercialization of wearable and implantable biomonitoring sensors and actuators, as well as to promote their adoption in clinical settings, especially in resource-limited areas.

SUMMARY

The present invention provides novel omniphobic paper-based smart bandage devices, and methods to make and use the omniphobic paper-based smart bandage devices.

In one embodiment, the present disclosure provides a wearable and/or implantable epidermal paper-based electronic device, wherein the device comprises:
   an electrically conductive layer; and
   a paper layer with a first hydrophilic side and a second omniphobic side,
   wherein the electrically conductive layer is attached to the first hydrophilic side of the paper layer.

In another embodiment, the present disclosure provides methods of preparing and using the wearable and/or implantable epidermal paper-based electronic device.

DETAILED DESCRIPTION

Figure 1:
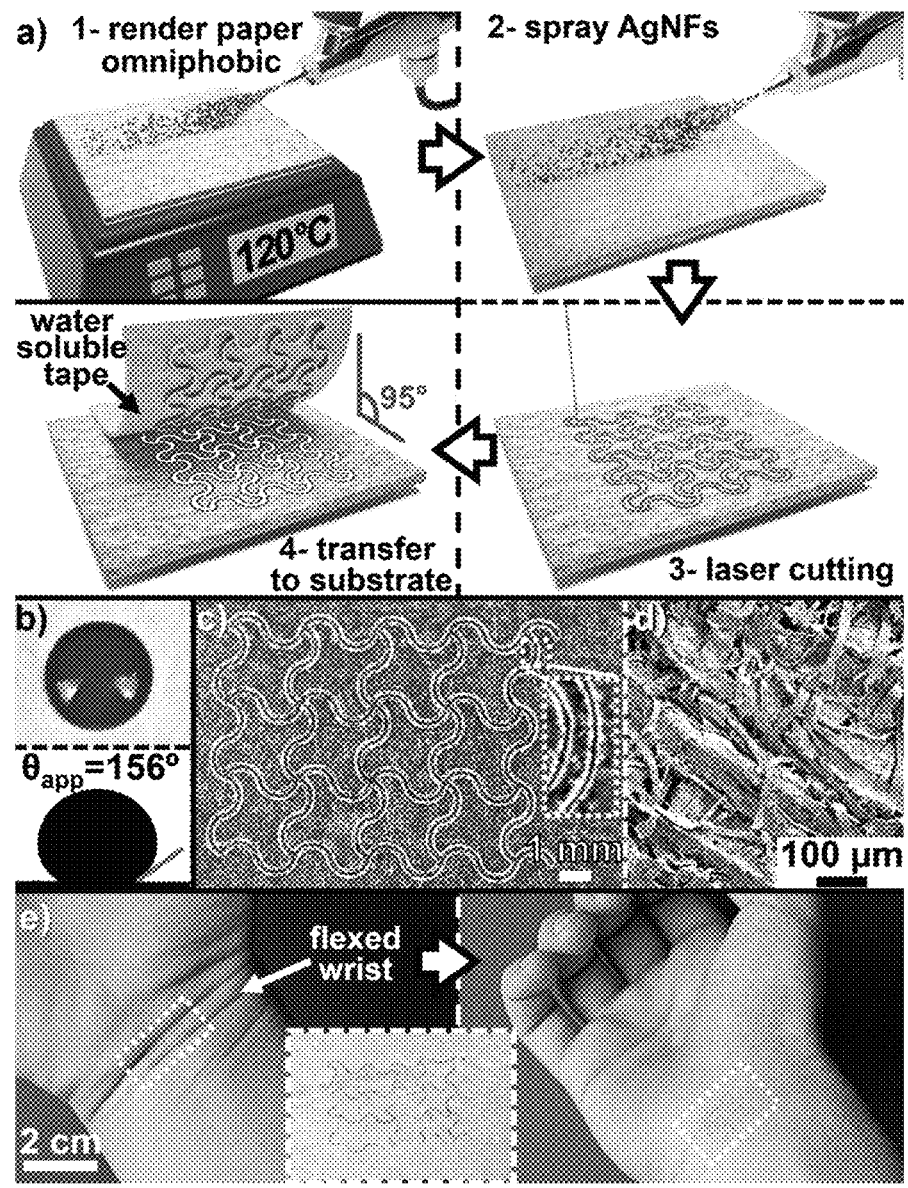
FIG. 1: EPED fabrication process and integration onto skin. (a) Schematic diagram of the fabrication of EPEDs: (1) Rendering one side of the paper omniphobic by spraying a silanizing solution over a hot plate; (2) Spray deposition of AgNFs over the other (hydrophilic) side of the paper; (3) Laser cutting the geometry of the EPED; (4) Transferring EPED onto skin using water-soluble tape (Video S1). (b) Representative images of a 10 μL drop of blood on silanized paper exhibiting a static contact angle ($\theta_{app}$) of 156°. (c) Optical image of an EPED with a thickness of 70 μm and an electrode width of 150 μm prior to its transfer onto temporary water-soluble substrate. (d) Representative scanning electron microscopy (SEM) image of the omniphobic side of the EPED. (e) EPED shown in (c) integrated onto the skin of the wrist undergoing compression (left) and stretching (right). The enlarged inset image highlights the intimate contact maintained between the skin and the EPED during repeated mechanical deformations.

For the purposes of promoting an understanding of the principles of the present disclosure, reference will now be made to embodiments illustrated in drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

In the present disclosure the term "omniphobic" refers to certain characteristics of a material that is both hydrophobic and oleophobic and capable of repelling various types of liquids such as water, oil, and as well as other contaminants. In one aspect of this disclosure regarding an omniphobic paper, the omniphobic paper is fabricated by applying certain fluorinated alkyltrichlorosilane to a paper substrate. In one aspect, the fluorinated alkyltrichlorosilane may be but is not limited to $CF_3(CF_2)_5(CH)_2SiCl_3$ or trichloro-(1H,1H,2H,2H-perfluorooctyl)silane.

In one embodiment, the present disclosure provides a wearable and/or implantable epidermal paper-based electronic device, wherein the device comprises:
an electrically conductive layer; and
a paper layer with a first hydrophilic side and a second omniphobic side,
wherein the electrically conductive layer is attached to the first hydrophilic side of the paper layer.

In one embodiment of the present disclosure regarding the device, wherein the device further comprises a detachable or soluble layer configured to facilitate the manipulation and/or transfer of the wearable or implantable epidermal paper-based electronic device, wherein the detachable or soluble layer is attached to the second omniphobic side of the paper layer.

In one embodiment of the present disclosure regarding the device, wherein the electrically conductive layer is patterned in highly stretchable shape.

In one embodiment of the present disclosure regarding the device, wherein the electrically conductive layer is configured to be mounted on skin of a wearer and be used to measure electrophysiological signals of the wearer.

In one embodiment of the present disclosure regarding the device, wherein the electrically conductive layer is configured to be mounted on skin or be implanted in body of a subject and be used to provide thermal stimulation on underlying tissue of the subject.

In one embodiment of the present disclosure regarding the device, wherein the electrically conductive layer may be stencil printed and/or razor printed.

In one embodiment of the present disclosure regarding the device, wherein the electrically conductive layer may be but is not limited to metals, metallic nanoparticles, metallic alloys, conductive polymers, organic conductors, conductive ceramic, nanoparticles, ionic solutions, semiconductors, liquid metals, conductive textiles, conductive foams, conductive inks, or any combination thereof. In one aspect, the electrically conductive layer may be made of Ag/AgCl ink, carbon ink, or a combination thereof.

In one embodiment of the present disclosure regarding the device, wherein the electrically conductive layer may comprise more than one independent pieces configured to serve as measuring, ground, and/or reference electrodes for measuring electrophysiological signals of a subject to be tested.

In one embodiment, the present disclosure provides a method of preparing a wearable and implantable epidermal paper-based electronic device, wherein the method comprises:
    providing a sheet of hydrophilic paper with a first and a second side;
    treating the first side of the hydrophilic paper with a silanizing material to make the first side omniphobic;
    providing an electrically conductive material to the second side of the hydrophilic paper;
    fabricating the device to provide a highly stretchable form; and
    providing a water-soluble tape to attach to the first side of the hydrophilic paper that is treated with the silanizing material to transfer the fabricated device to the water-soluble tape.

In one embodiment, the present disclosure provides a method of using the wearable and implantable epidermal paper-based electronic device of the present disclosure, wherein the method comprises:
    treating a subject skin with a medical glue;
    attaching the wearable and implantable epidermal paper-based electronic device to skin of the subject, wherein the second side of the hydrophilic paper with the electrically conductive material is in contact with the skin; and
    using water to rinse off the water-soluble tape to allow the wearable and implantable epidermal paper-based electronic device to attach to the skin without the water-soluble tape.

Materials and Methods

Materials

The following paper substrates were used in this study: TX609 (Texwipe Inc.), OLAA0059 (Navigator, Inc.), 58115 (Kimberly-Clark, Corp.), AC9165 (DowDuPont, Inc.), OCB2000 (DRL Enterprises Inc.), ELE-300 (Elements Inc.), and WAH1001 (GE Healthcare, Inc.). Calendered TX609 is labeled as C-TX609.

Thin copper foils (20-μm-thick, Kraftex Products, Gloucestershire, UK) and Ag/AgCl ink (AGCL-675, Applied Ink Solutions, Westborough, MA, USA) were employed as conductive layers.

A solution of a long-chain fluorinated organosilane (Di-isopropyl(3,3,4,4,5,5,6,6,7,7,8,8,9,9,10,10,10-heptadecafluorodecyl)silane, Sigma-Aldrich Corp., St. Louis, MO, USA) was used to render the paper substrates omniphobic.

Fabrication of Ag/AgCl-based EPEDs

FIG. 1 illustrates the fabrication process of Ag/AgCl-based EPEDs. Silanized 3 cm×3 cm paper substrates were used to fabricate EPEDs by placing the paper on a hot plate at 120° C. in a chemical hood at room temperature and spraying its top surface with a 4.3% v/v solution of a highly fluorinated alkylsilane (3,3,4,4,5,5,6,6,7,7, 8,8,9,9,10,10,10-heptadecafluorodecyl trichlorosilane ($CF_3$ $(CF_2)_7$ $CH_2$ $CH_2$ $SiCl_3$, "$C_{10}{}^F$")) in isopropanol. After the silanizing agent dried, the other side of the paper was sprayed with ~500 μL of a 5-10 wt. % suspension of AgNFs (Inframat Advanced Materials, LLC) in toluene and let it dry in a desiccator at 36 Torr for 10 min. The open mesh serpentine layout of the EPEDs was designed using AutoCAD 2016 (Autodesk, Inc.). This provided EPEDs with ~1.05 $cm^2$ top surface area and a ~15 μm thick conductive layer where the cellulose fibers are coated with a layer of AgNFs ~3-5 μm thick (~5 mg of AgNFs per device). The minimum linewidth of the serpentine layout was kept at 150 μm, the minimum resolution of the $CO_2$ laser (MT-3050D, 60 W, MornTech, USA) use to shape the EPEDs. Water-soluble tape was used to transfer EPEDs onto skin previously sprayed with a breathable and waterproof medical glue (Nexcare, 3M, Inc.).

Fabrication of Copper-Based EPEDs

Figure 2:
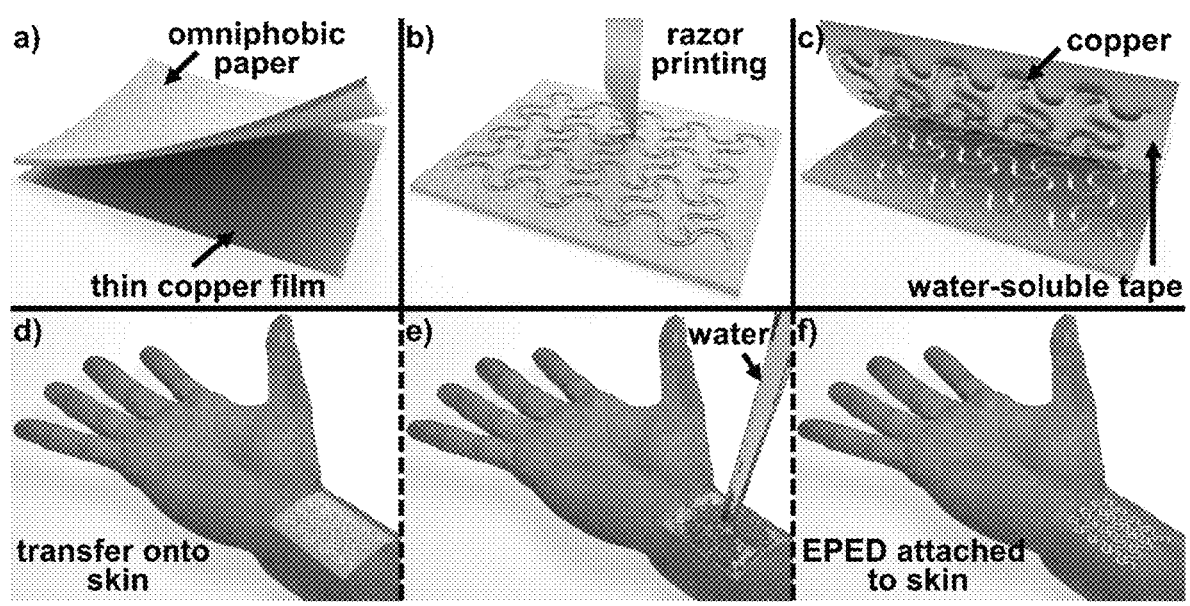
FIG. 2: Fabrication of epidermal paper-based electronic devices (EPEDs) using razor printing: (a) A layer of omniphobic paper is glued to a thin metallic film that serves as a conductive layer (alternatively Ag/AgCl ink can be directly deposited on omniphobic paper); (b) A 100-μm-thick razor blade shapes the ensemble into a serpentine pattern; (c) A water-soluble tape, attached to the paper side of the EPED, is used as a temporary substrate for transfer onto skin; (d) The EPED is transferred onto skin previously sprayed with medical glue; (e) Placing the EPED under a stream of running water dissolves the temporary substrate; (f) EPED conformally attached to the skin.

FIG. 2 illustrates the fabrication process of copper-based EPEDs. The paper substrates were functionalized by spraying the organosilane solution at ambient conditions and letting it dry in a desiccator at 36 Torr for 20 min. The open mesh serpentine layout of the EPEDs was designed using Adobe Illustrator CC (Adobe Systems Inc., San Jose, CA, USA) according to geometries previously reported in [10, 11]. The minimum line width of the serpentine layout was kept at 200 μm (FIGS. 1b and 2b), the minimum resolution of our programmable razor printer (Silhouette Cameo™, Silhouette America Inc., Lindon, UT, USA), which uses a 100-μm-thick blade as the cutting tool. Prior to shaping the serpentine layout of the EPEDs, adhesive copper tape (for copper-based EPEDs) was attached to the functionalized paper. These functionalized paper substrates covered with a conductive layer (thickness of the composite ranging 70-190 μm) were then attached to a water-soluble tape (Aquasol Corp., North Tonawanda, NY, USA), which acted as the transfer layer to mount the EPEDs on skin (FIG. 1c-f). Prior to the placement of EPEDs on skin, we sprayed medical glue (Medique products, Fort Myers, FL, USA) over the skin to maintain the conformal contact of the EPEDs on stretching. The transfer layer was then dissolved under a stream of running water.

Wirelessly Powered EPEDs

Wirelessly powered optoelectronic EPEDs were assembled by soldering an EPED antenna using a small amount of low melting point soldering paste (Chip Quik SMD291AX) to a miniaturized half-wave rectifier. A vector network analyzer (E5071B ENA, Agilent Technologies) was used to find the resonant frequency of these EPEDs. A copper coil (18 AWG wire, 6 turns, 5 cm diameter) was used to wirelessly power EPEDs by exciting their resonant frequency with a sinusoidal signal generated by a waveform generator (DG4062 Series, RIGOL Technologies Inc.). All EPEDs were characterized passively at a distance of 15 cm from the center of the coil, in an orientation perpendicular to the axis of the coil.

The network analyzer was programmed to record the real and imaginary parts of the impedance at 1601 frequency points linearly spaced in the range 1-20 MHz, finding the resonant frequency of the EPED using the min-phase method. To enable the wireless powering of EPEDs, the coil was excited at the resonant frequency with a sinusoidal signal generated by a waveform generator (DG4062 Series, RIGOL Technologies Inc., Beaverton, OR, USA).

Mechanical Characterization

Stress-strain characteristics of paper substrates as well as fabricated EPEDs were acquired with a universal testing machine (MTS insight 10, MTS Systems Corp.) using a 100 N load cell (model 661.18.F01), following ASTM D828-16 specifications. A loading rate of 10 mm/min was applied by fixing the gage length to 50 mm for paper substrates; while for the EPEDs, a gage length of 10 mm (comparable to the size of the device) and a loading rate of 5 mm/min was used.

Finite Element Analysis

Abaqus/CAE 6.13-1 (Simulia, Corp.) was used to simulate the distribution of maximum principal strains and von Mises stresses over the EPEDs. The material characteristics used in the simulations were obtained experimentally from the uniaxial tensile tests of the different papers. The failure of the EPED is modelled by the ductile damage method using hexagonal C3D8R elements to obtain 3D stress distributions with controlled distortion.

Implantable EPEDs

Implantable EPEDs were tested in vivo on laboratory mice (C57B6J, 8-15 weeks old, male) with mixed backgrounds. Prior to implantation, the EPED was encapsulated in a biocompatible matrix by spraying both of its sides with a 5 wt. % Polydimethylsiloxane (PDMS, Sylgard 184, DowDuPont, Inc.) solution in toluene. After spraying each side of the EPED, the resulting PDMS layer was cured at 60° C. for 2 h. The mice were anaesthetized using a ketamine xylazine cocktail (0.1 g per kg of body weight) before implantation. The thermal distribution created by the EPEDs was imaged using an IR camera (FLIR-E8, thermal sensitivity=0.05° C., FLIR, Inc.). All procedures involving mice were performed in accordance with Purdue University's Animal Care and Use Committee.

Measurement of Physiological Signals

ECG, EMG, and EOG signals were collected using three EPED electrodes (reference, measurement, and ground) from a volunteer with signed consent. A commercial electrophysiological recorder (Backyard Brains, Inc.) controlled by a portable open-source microcontroller (Arduino, Inc.) was connected through 28 AWG cables to the EPEDs to amplify and filter the signals. The performance of EPEDs was compared to that of conventional gel electrodes (Medline Industries Inc.) by placing these electrodes in the same position as the EPEDs and ensuring their electrical contact with skin using conductive electrode gel (SPECTRA® 360, Parker Laboratories Inc.).

The thickness of the medical glue layer deposited on the skin is <2 μm, minimally affecting the performance of the EPED while recording physiological signals.

To perform underwater experiments, an extra layer of medical glue was deposited over the skin to encapsulate the flat connection between the EPEDs and the cables. Any excess of medical glue sprayed on the skin accumulated along the lateral walls of the EPED, preventing those exposed areas of the conductive layer from short-circuiting while under water.

Heat Therapy Using EPEDs

EPEDs with copper and Ag/AgCl ink were used as the conductive layers to apply heat uniformly to the skin of the user. The thermal distribution created by the EPEDs was imaged using an infrared (IR) camera (FLIR E8, Wilsonville, OR, USA). A DC power supply (DP832A, RIGOL Technologies Inc., Beaverton, OR, USA) was used to generate heat through the resistive EPED, applying power levels below FCC guidelines (<2 W). To ensure the accuracy of the real-time monitoring of the temperature of the skin, the distance between the IR camera and the EPED fixed was kept at 20 cm during all the experiments.

Scanning Electron Microscopy (SEM)

A scanning electron microscope (Nova NanoSEM 200, FEI, Hillsboro, OR, USA) was used to examine the structure of the fabricated EPEDs. Before imaging, a sputter coater (208HR, Cressington, UK) was used to create a uniform conductive coating of ~10 nm platinum, using a D.C. current of 40 mA for 60 s. SEM images of the samples were captured at an electron accelerating potential of 5 kV, spot size 3, and working distance of 5 mm using an Everhart-Thornley detector (ETD).

Results and Discussion

FIG. 1a shows the fabrication process followed to make EPEDs on a single layer of cellulose paper (~70 μm thick). One side of the paper was first rendered omniphobic by spraying a 4.3% v/v solution of a long-chain fluorinated organosilane ($C_{10}^F$) in isopropanol, while the paper is placed on a hot plate at 120° C. inside a chemical hood. The heat from the hot plate evaporates the solvent of the sprayed $C_{10}^F$ solution, preventing the cellulose fibers ~15 μm away from the heat source from interacting with the silane. After 30 s, the solvent impregnating the cellulose fibers on the top side of the paper evaporates, completing the silanization process. The modified paper exhibits an apparent static contact angle of ~156° with complex solutions like blood over a thickness of ~55 μm on its omniphobic side (FIG. 1b), remaining hydrophilic on the other side. The hydrophilic side of the paper was sprayed a 5-10 wt. % suspension of Ag nanoflakes (AgNFs) in toluene and let it dry in a desiccator at 36 Torr for 10 min. The hydrophilic cellulose fibers coated with AgNFs ~3-5 μm thick serve as the electrically conductive layer of the EPED, exhibiting high electrical conductivity even during flexing and creasing (resistivity as low as 60 nΩm, without requiring a sintering process). Laser cut the layout of the EPEDs in a stretchable form—such as open mesh serpentine designs (FIG. 1c)—and used water-soluble tape to separate them from the paper substrate (lifting the tape at a ~95° angle) and transfer them onto skin previously sprayed with medical glue (spray-on-bandage). The sprayed layer of medical glue used to secure the EPED to the skin of the user is partially absorbed by the porous conductive layer of the EPED, preventing the delamination of the AgNFs. After the transferring tape is dissolved in water, the thin layer of medical glue secures the mechanical contact between the conductive layer of the EPED and the skin, without significantly constraining the motion of the wearer or hampering the acquisition of electrophysiological measurements (FIG. 1e).

Paper was used to fabricate EPEDs because it is inexpensive, breathable, easy to silanize, and readily and universally available in a wide variety of porosities and thicknesses. Additionally, cellulose fibers exhibit an average diameter of ~10-20 μm and are oriented and entangled at random directions, which allows the laser cutter to trim paper in serpentine designs with isotropic mechanical properties. While the proposed fabrication method is compatible with fabrics, their structure, typically composed of yarns of fibers with diameters ≥100 μm knitted in a particular direction, makes laser cut fabric-based serpentine designs to come apart when they are stretched. New "paper-like" synthetic fabrics fabricated using electrospun fibers have demonstrated to outperform paper in several bioanalytical and microfluidic applications due to their better mechanical properties, however, the extensive number of variables that need to be optimized to obtain fibers with appropriate sizes (molecular weight of the polymer, surface tension, flow rate, temperature, voltage, distance between the fiber collector and the extruder, . . . ) often increase the complexity of the fabrication of these synthetic fabrics.

Figure 3:
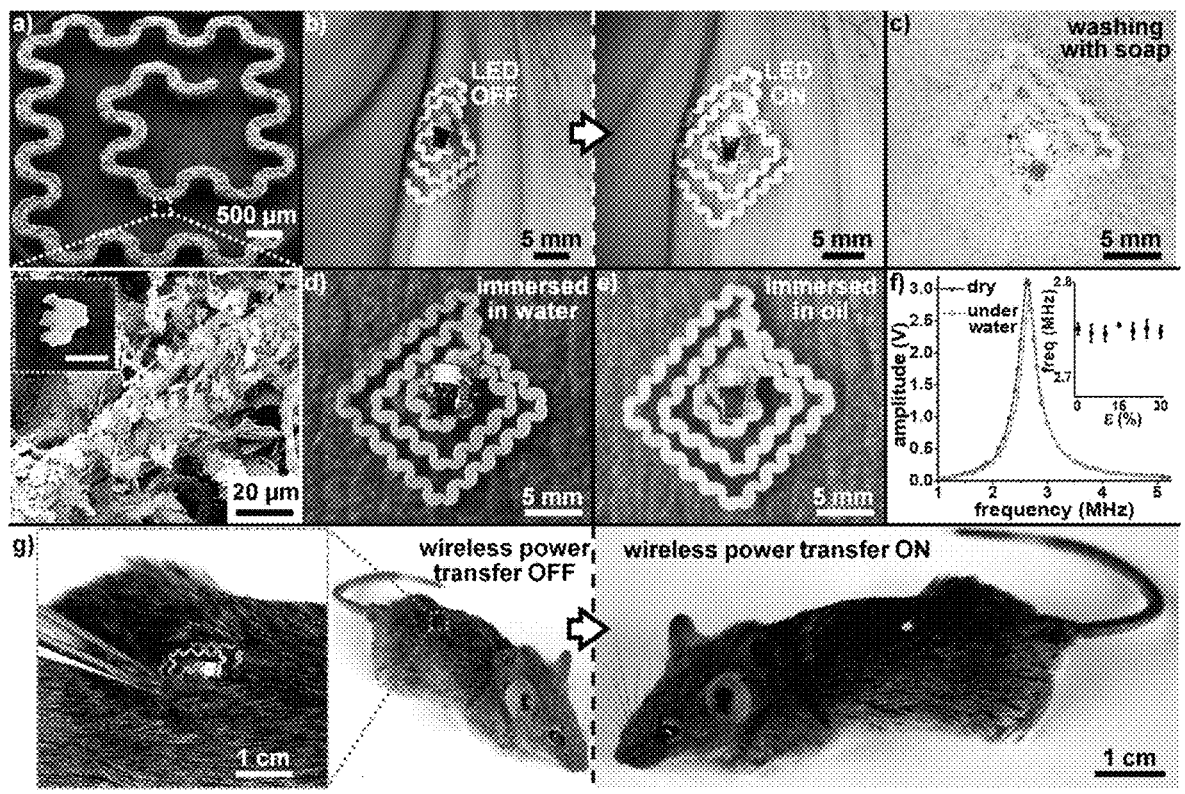
FIG. 3: Wearable and implantable EPED capable to provide wirelessly powered optical stimulation. (a) Top: SEM image of a paper-based serpentine antenna (omniphobic side up). Bottom: SEM image of the conductive side of the antenna showing how the AgNFs adhere to the cellulose fibers of the paper without blocking its porous structure, preserving its breathability. The inset shows a high-resolution image of a silver nanoflake (scale bar is 2 μm). (b) Optical image of an EPED comprising an omniphobic paper-based antenna, a rectifying circuit, and an orange LED attached onto the skin of the wrist, under compression, before (left) and after (right) the activation of the wireless power transfer system. (c-e) Optical images showing the resistance to washing with soap and water (over 50 times), immersion in water (over 1 h), and immersion in oil (over 1 h) of EPEDs provided by the omniphobic character of the thin paper-based antenna. (f) Frequency response of the wireless optoelectronic EPED in air and under water. Inset shows the stable resonant frequency of the EPED as a function of strain. (g) Wireless optoelectronic EPED implanted in a 32 g mouse for optogenetic applications.

Since the sprayed AgNFs adhere to the surface of the individual cellulose fibers (FIG. 3a), the conductive layer of the EPEDs preserves the porous structure and breathability of omniphobic paper. To prevent the delamination of the EPEDs from skin due to their interfacial stiffness mismatch, a thin layer of breathable medical glue was sprayed to the skin. The glue ensures that the conductive layer of the EPED is efficiently attached to the skin of the user without affecting the omniphobicity of the rest of the EPED. Breathable EPEDs with a thickness of 70 μm provide an itch-free and comfortable attachment to the skin, inducing a minimal somatosensory perception of these paper-based devices due to their bendability and stretchability. The fibrous structure of the conductive layer of the EPEDs facilitates the attachment of electronic components—using low melting point solder—to extend their functionality. Although the resolution of the laser cutting system enables the fabrication of EPEDs with electrode widths of 150 μm (FIG. 1e) and a ~90Ω resistance between diagonally opposite corners, EPEDs with wider serpentine paths (electrode width ~300-700 μm) exhibit lower resistance values (~20-50Ω) and are more appropriate in applications benefiting from low ohmic losses, such as far-field wireless power transfer (FIG. 3b-3g) and the measurement of electrophysiological signals. The omniphobic paper substrate of the EPED (facing up) and the breathable and waterproof medical glue used to attach the conductive layer of the EPED to the skin prevent AgNFs from oxidizing under water during washing (FIG. 3c). As a consequence, EPED antennas can function during prolonged immersion (1 h) in oil or water (FIG. 3d), without significant shift in their resonance frequency (FIG. 3f). The frequency response of EPED antennas remains relatively stable under elastic strains up to 30% due to the mechanical reinforcement of the conductive layer of the EPED provided by the omniphobic paper substrate (FIG. 3f inset). Wireless EPEDs equipped with LEDs can be implanted and tested in vivo (FIG. 3g), after their encapsulation in a biocompatible polymer (polydimethylsiloxane, PDMS), making them useful for applications involving optogenetic stimulation. The encapsulation of EPEDs in PDMS ensures that no AgNFs will be released by the conductive layer of the EPED, preserving the biocompatibility of the device. This flexible encapsulation, however, significantly reduces the breathability of the EPED, which, while not required for implantable devices, is highly beneficial in epidermal electronic applications.

Figure 4:
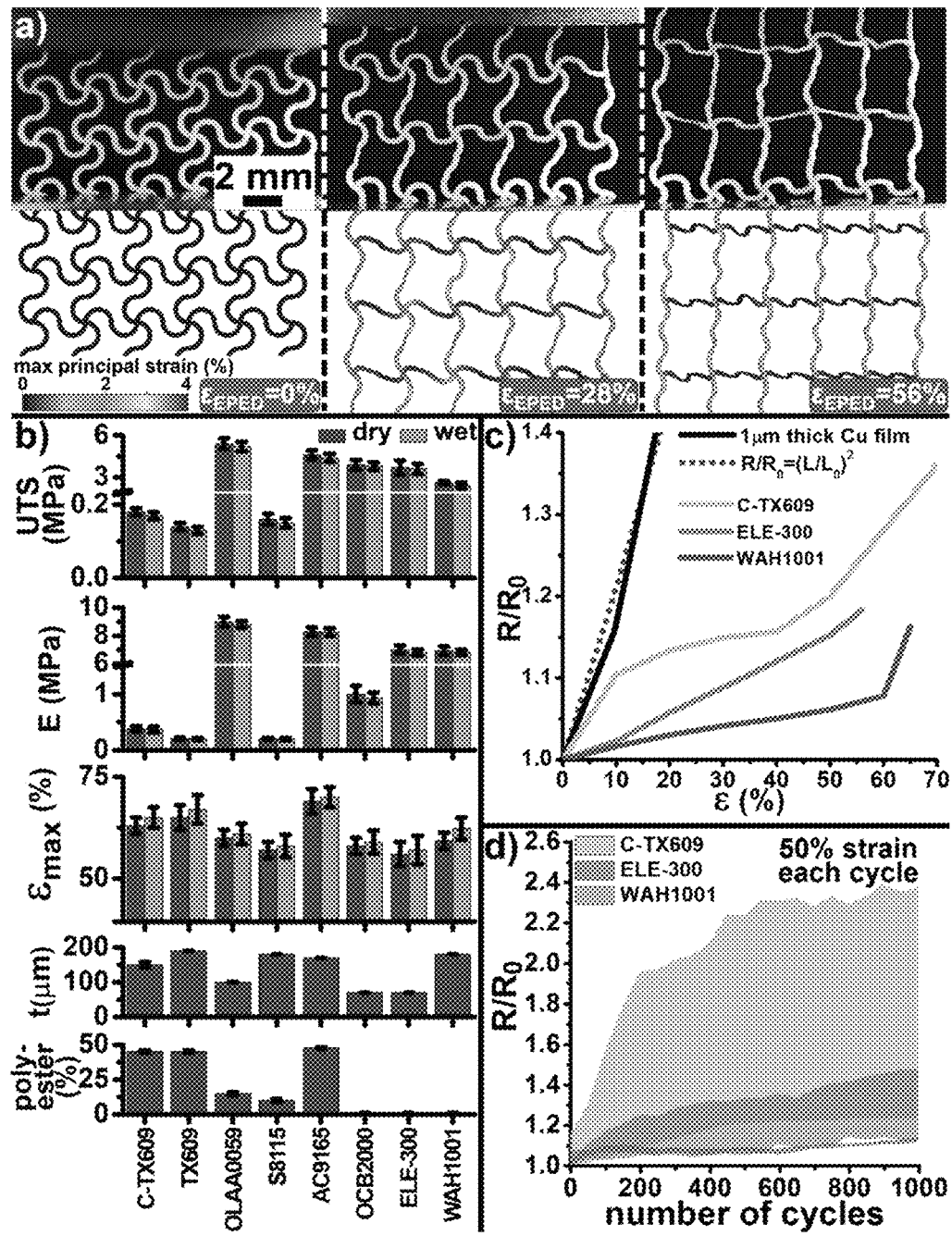
FIG. 4: Mechanical properties of EPEDs under stretching. (a) Top: Snapshots from Video S4 showing the geometry of 70 µm thick EPED after applying uniaxial tensile strains of 0% (left), 28% (middle), and 56% (right). Bottom: FEA contour plots of the maximum principal strain distribution on the EPED at those uniaxial strains. (b) Concentration of polyester fibers, thickness, maximum strain, effective Young's modulus, and ultimate tensile strength of EPEDs fabricated using different cellulose-based papers, in dry and wet conditions. (c) Comparison between the normalized resistance-strain curves of EPEDs fabricated on C-TX609, ELE-300, and WAH1001, and the normalized resistance-strain curve of a Cu thin film-based EES mounted on an elastomeric slab, which matches the theoretical curve $R/R_0 = (L/L_0)^2$.

FIG. 4a shows that conformable 70 μm thick EPEDs can be stretched up to 56%, without any evidence of cracks, fractures, or plastic deformations, due to the mechanical strength of the omniphobic cellulose fibers of the EPED. The large stretchability of EPEDs in comparison with human skin ($\varepsilon_{skin,max} \cong 28\%$) and their similar Young's moduli (203 KPa for EPEDs fabricated with C-TX609; FIG. 4b), facilitates the use of EPEDs as on-skin monitoring systems without causing significant constraints to the natural movements of the user. The experimental results are in good agreement with the distribution of the maximum principal strains over the EPED shown by the finite element analysis (FEA, details in Experimental Section), since the maximum principal strains in each of the trace units of the EPED are below the facture limit of omniphobic paper (~4%; FIG. 4a). When compare EPEDs with traditional thin film-based EES (1 μm thick Cu layer patterned with the same serpentine design and mounted on an elastomeric slab), maximum principal strains greater than ~11% lead to the breakage of the structure after ~20-40% stretching. FIG. 4b shows the mechanical properties of EPEDs fabricated using different commercially available papers. These mechanical tests were performed by using both "dry EPEDs" (relative humidity 45%) and "wet EPEDs" (EPEDs immersed in water at 25° C. for 30 min prior to their mechanical characterization). While the mechanical properties of untreated cellulose-based papers are very sensitive to environmental moisture, the silanization step used to render EPEDs omniphobic makes their mechanical properties insensitive to humidity (FIG. 4b).

Before the formation of cracks upon elongation, thin film-based EES with serpentine layouts exhibit resistance-strain curves following $R/R_0 \approx (L/L_0)^2$, where $R/R_0$ and $L/L_0$ are the normalized resistance and length, respectively (FIG. 4c). Under similar strains, the normalized resistances of EPEDs are lower than those of EES, since the fibrous structure of the EPEDs accommodates deformation during stretching and prevents the initiation and propagation of cracks on the device. FIG. 4d shows that EPEDs fabricated in 100% cellulose paper (ELE-300, for example) maintain a good electrical performance upon repetitive elongation, exhibiting minimal degradation after repeated straining of 50% (enough to break a Cu thin film-based EES) over 1000 stretch-release cycles. On the other hand, EPEDs fabricated with cellulose paper substrates containing 45% polyester (C-TX609, for example) exhibit a lower effective Young's modulus than those fabricated with 100% cellulose paper and can withstand larger deformations before breaking (Eurax up to 68%). EPEDs fabricated with polyester/cellulose blend papers, however, exhibit resistance values more sensitive to strain (FIG. 4c, 4d).

Figure 5:
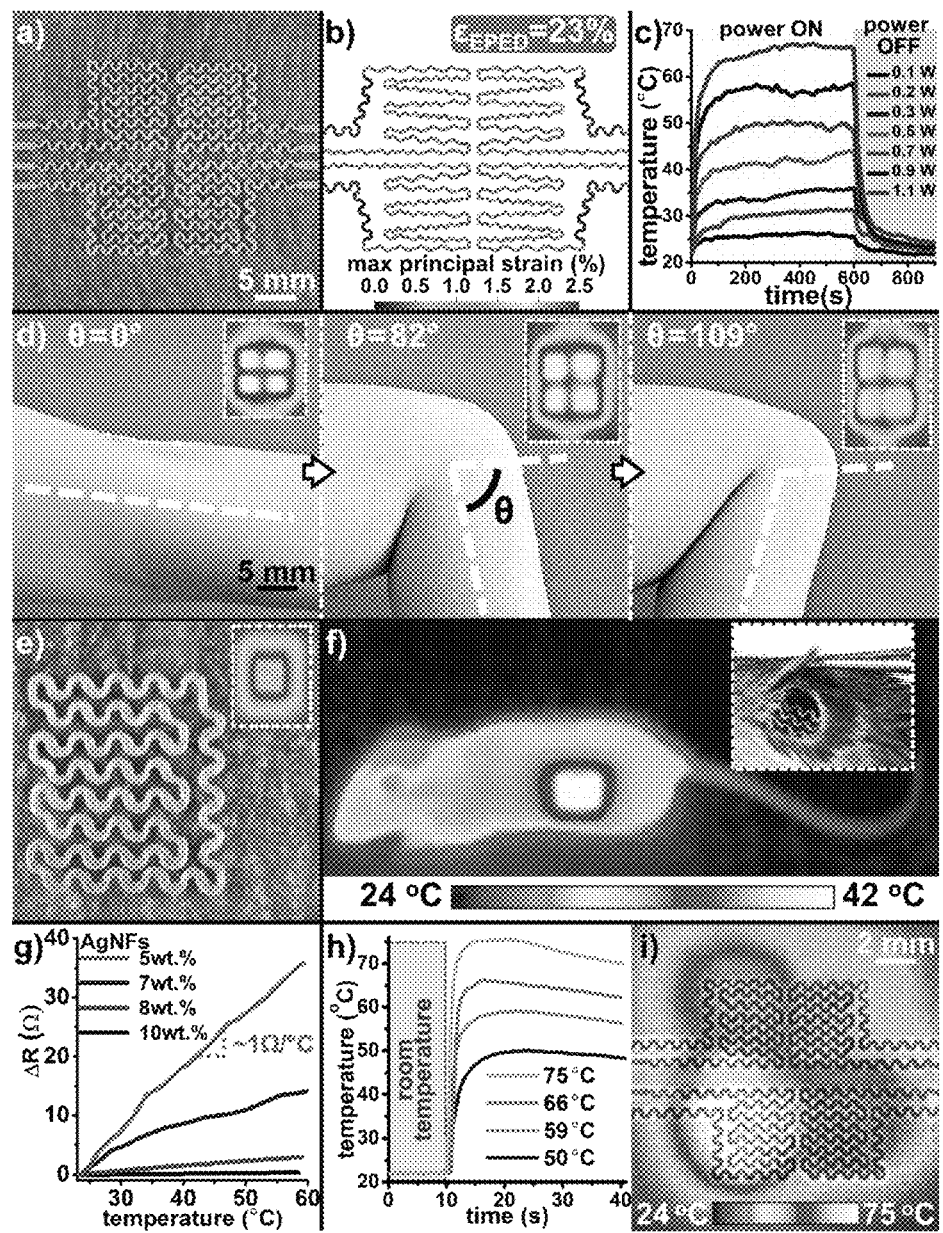
FIG. 5: Wearable and implantable EPEDs used as a conformable 2×2 array of temperature sensors and as a thermotherapy patch. (a) Representative optical image of a thermopatch with four independent heating elements attached to skin. (b) FEA simulation showing the deformation of the thermopatch after applying a strain of 23% to the EPED. (c) Experimental temperatures induced by the thermopatch for applied powers ranging from 0.1-1.1 W. (d) Optical snapshots and IR images (insets) of the thermopatch mounted on the elbow and subjected to three different bending angles (θ=0°, 82°, and 109°). (e) Optical image of a wireless paper-based thermopatch. Inset shows the IR heat map (maximum temperature is 42° C.) generated by the EPED when wirelessly powered. (f) Localized heat therapy applied to the inguinal adipose tissue of a 32 g mouse by powering the EPED wirelessly at its resonant frequency (5.5 MHz). (g) Absolute change of resistance of the EPED shown in (a) as a function of external temperature for different concentrations of sprayed AgNFs. ΔR=0 at room temperature (23° C.). See Figure S13 for relative changes in resistance. (h) Experimental temperature mapping performed with a 2×2 array EPED placed on a thermally insulating foam (t=0 s). At t=10 s, four different Al cylinders, preheated to 50, 59, 66, and 75° C., were placed on top of each quadrant of the EPED. Temperature values are calculated from the absolute increments of resistance (Figure S14) of the electrodes according to the 5 wt. % AgNFs calibration curve in panel (g). (i) IR image captured after removing the Al cylinders from the EPED.

FIG. 5a shows a thermotherapy EPED patch with four independent heating elements (resistance ~2Ω, thickness=70 μm). The serpentine layout of this thermotherapy patch yields elastic responses to induced strains (FIG. 5b), accommodating natural motions of the skin without significant mechanical constraint or interface delamination. The Joule heat dissipated by this EPED is linearly proportional to the power applied through an external wire connection, facilitating the controlled operation of each of the heating elements of the thermotherapy patch (FIG. 5c). FIG. 5d shows the application of therapeutic heat to the elbow under bending (θ=0–109°) using this EPED. An IR camera was used to verify that the temperature applied to the joint was maintained in the range 39-42° C. (external power=0.5 W). The mechanical reinforcement upon stretching provided by the omniphobic paper substrate to the conductive layer of the EPED enables these low cost devices (~0.06 USD) to continuously apply heat to the elbow, even when it is completely bent (θ≈109°), whereas typical thin film-based devices with similar designs fail under bending angles of θ≈60° due to plastic deformation. FIG. 5e shows a thermotherapy EPED—with a single heating element—compatible with wireless powering via inductive coupling. Prior to the implantation of this EPED in a 32 g mouse (FIG. 5f), the EPED was encapsulated in PDMS by spraying both sides of the device with a 5 wt. % solution of PDMS in toluene. The thin layer of PDMS encapsulating the EPED ensures its biocompatibility over a 10-day period, preserves the flexibility of the implantable device, and prevents the delamination of the AgNFs from the conductive layer of the EPED. Upon wireless power transfer (5.5 MHz), the implanted EPED provides localized heat (up to 42° C.) to the inguinal adipose tissue of the mouse without mechanically constraining the motion of the animal. We tested the operation of this EPED during 10 days without experiencing any significant change in the resonant frequency or the generated temperature.

FIG. 5g and FIG. 5h show that the predictable change in resistance of the conductive layer of the EPEDs due to changes in the environmental temperature makes it possible to extend the applications of the thermopatch to temperature sensing. The dependence of the resistance of the EPED was characterized on the environmental temperature, without applying any mechanical strain, obtaining a sensitivity of ~1 $\Omega°$ C.$^{-1}$ for EPEDs with a conductive layer fabricated by spraying a 5 wt. % suspension of AgNFs. The arrangement of multiple paper-based temperature sensors in arrays also enables spatial mapping of temperature. FIG. 5h shows the experimental temperature mapping generated by an EPED with a 2×2 array of temperature sensors when four different Al cylinders preheated to 50, 59, 66, and 75° C. were placed on top of each of the quadrants of the EPED at t=10 s. The temperature measurements provided by each of the sensing elements of the EPED match well with the results obtained using an IR camera (FIG. 5i). The mechanical strains caused by the natural motion of the wearers could affect the resistance of the conductive layer of the EPED (FIG. 4c); therefore, the calibration of strain and temperature for each EPED design would be necessary to compensate for the correlation between the change in resistance and the environmental temperature.

Figure 6:
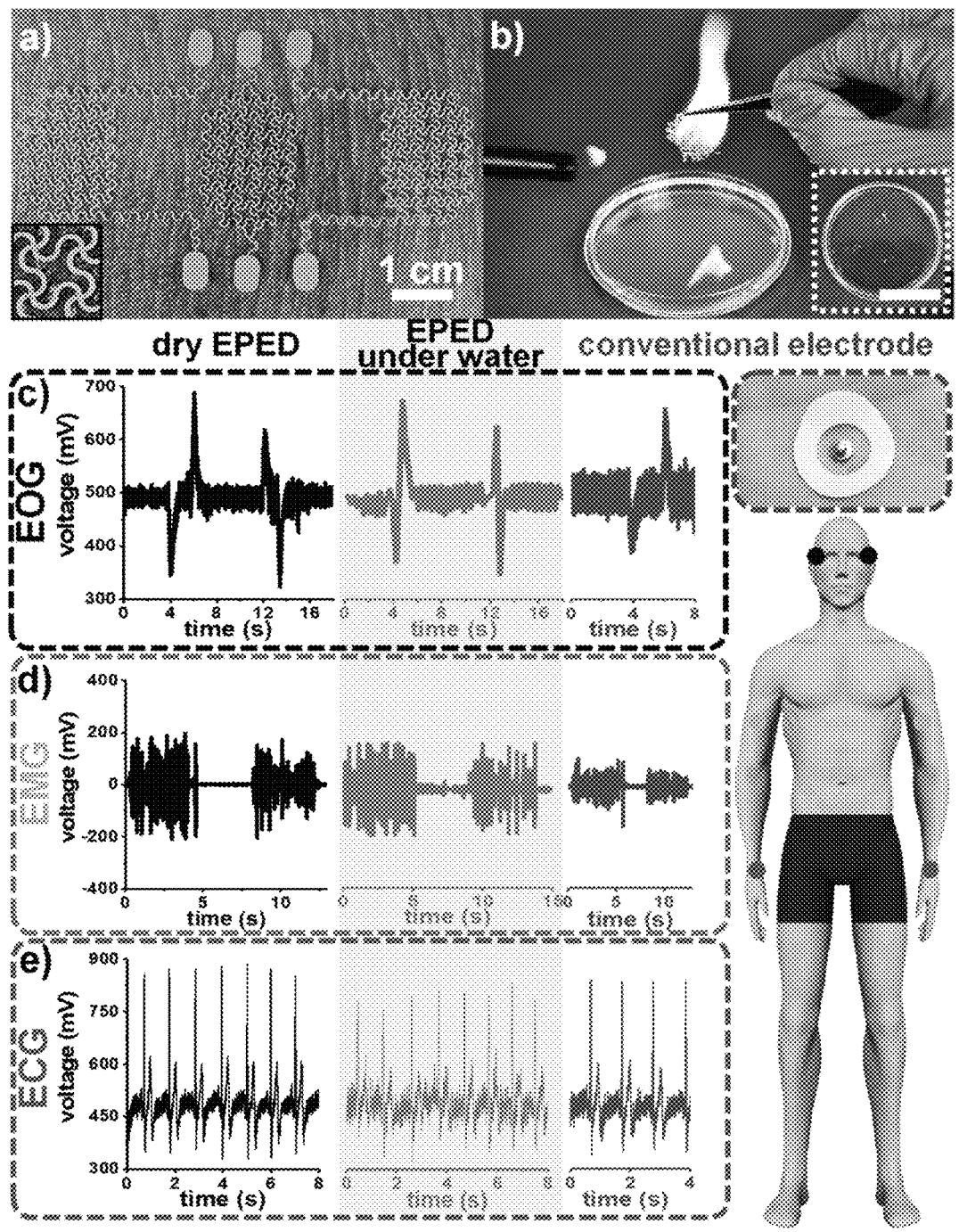
FIG. 6: Three-electrode EPED use to monitor electrophysiological signals in ambient conditions and under water. (a) From left to right: Measuring, ground, and reference electrodes mounted on skin. The inset shows the unit cell of the serpentine design with a trace width of 250 µm and thickness of 70 µm. (b) Disposability of the EPED shown in (a) by incineration. The inset shows remnants of disposed EPED. The scale bar is 5 cm. (c) EOG signals obtained with the three-electrode EPED in ambient conditions (left) and under water (center). EOG signals obtained with conventional gel electrodes (right) are provided for comparison. The black solid circles on human model show the location of the electrodes to record EOGs. (d) EMG signals measured using an EPED mounted on top of the biceps (green solid circles) in ambient conditions (left) and under water (center). EMG recorded using gel electrodes (right) are provided for comparison. (e) ECG signals recorded using an EPED placed on the inside of the wrist (blue solid circles) in ambient conditions (left) and under water (center). ECG recorded using gel electrodes (right) are provided for comparison.

The low resistivity and high conformability of EPEDs to skin facilitate their use as low cost electrophysiological monitors. FIG. 6a shows an EPED with an open mesh serpentine design comprising a measurement, ground, and reference electrode. After their use, these 70 µm thick EPEDs can be easily removed from the skin, causing minimal irritation, by delaminating one of its ends with the nails and peeling the rest of device by pulling. Used EPEDs can be disposed by incineration, which oxidizes the AgNFs (<5 mg/device) and produces minimal amounts of solid by-products (FIG. 6b). The performance of these paper-based electrophysiological monitors was studied in ambient conditions and under water by recording electrooculograms (EOG), electrocardiograms (ECG), and electromyograms (EMG) from a volunteer (age 30) with these EPEDs placed on the forehead (FIG. 6c), wrist (FIG. 6d), and bicep (FIG. 6e), respectively. The omniphobic character of the EPEDs prevents the short-circuiting of their electrodes while under water, enabling the recording of accurate electrophysiological measurements independently of environmental moisture (FIG. 6c-e, blue color). When comparing the experimental results obtained with the EPEDs with those acquired using conventional gel electrodes (FIG. 6c-e, red color), it was observed that the mechanical conformability of the EPEDs to the skin significantly reduces the experimental noise, especially when the wearer moves. Additionally, conventional gel electrodes cannot be reliably utilized to capture electrophysiological signals under water due to the short-circuit of its terminals, swelling of the hydrogel, and subsequent delamination. The maximum strain at fracture of these EPEDs is $\varepsilon_{max} \approx 56\%$, higher than traditional Au thin-film based electrodes $\varepsilon_{max} \approx 35\text{-}45\%$.

Figure 7:
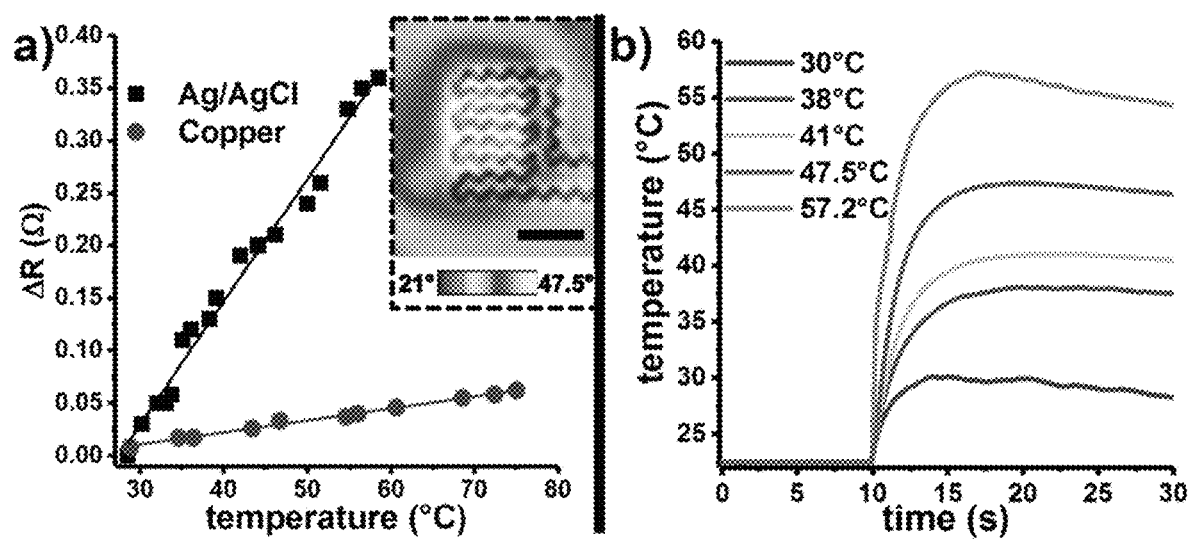
FIG. 7: Sensing temperature using EPEDs: (a) Change of the EPED resistance as a function of temperature for EPEDs with a thin copper film (solid red dots) and Ag/AgCl ink (solid black squares) as conductive layers. The inset shows an IR image of an Ag/AgCl-based EPED when a small aluminum cylinder at 47.5° C. is placed on its surface for 10 s and then removed. Scale bar is 5 mm; (b) Response of the Ag/AgCl-based EPED thermometers when an aluminum cylinder at different temperatures is placed in contact with the EPED at t=10 s.

The temperature dependence of the resistivity of the conductive layer of the EPEDs enables their use as wearable thermometers (FIG. 7). The linear relationship between the increment in resistance of the EPED and its temperature allowed us to calculate the sensitivity of Ag/AgCl- and copper-based EPED thermometers (FIG. 7a). The sensitivity of Ag/AgCl- and copper-based EPEDs are 0.01 $\Omega/°$ C. and 0.001 $\Omega/°$ C., respectively. The time response of the Ag/AgCl EPEDs was characterized by placing them over a surface at room temperature (t=0 s) and placing an aluminum cylinder preheated to different reference temperatures (t=10 s). It was observed that Ag/AgCl EPEDs required less than 1 s to reach reference temperatures in the clinically relevant range (FIG. 7b).

This disclosure provides simple, inexpensive, and scalable, fabrication of epidermal paper-based electronic devices (EPEDs). EPEDs fabricated using silanized paper can be used as moisture-insensitive epidermal electrodes, with a cost so low that it makes them compatible with single-use applications. EPEDs fabricated using copper film or Ag/AgCl ink are easy to mount on skin, conforming to its natural moves, and exhibit good mechanical contact with the user and a stable electrical performance upon stretching. Copper-based EPEDs exhibit low resistivity values (~20 nΩ m), enabling their use as efficient electrophysiological monitors, thermotherapeutic devices, and wirelessly powered systems. The low resistance of copper-based EPEDs, however, makes it difficult to detect changes in the resistance caused by environmental temperature. Ag/AgCl-based EPEDs have higher resistivity values (~110 nΩ m), facilitating their use as temperature sensors since small changes in the environmental temperature induce larger changes in the resistance of the devices. The fibrous structure of the paper substrates of the EPEDs makes them breathable when their conductive layer is porous, such as Ag/AgCl-based EPEDs. The adhesion of a continuous copper film to the paper, however, compromises the passage of gases across the EPED. The present disclosure demonstrates the omniphobic character of printed EPEDs by efficiently recording ECGs, EMGs, and EOGs in air and under water without any significant decrease in performance.

Additional disclosure is found in Appendix-A and Appendix-B, filed herewith, entirety of which is incorporated herein by reference into the present disclosure.

Those skilled in the art will recognize that numerous modifications can be made to the specific implementations described above. The implementations should not be limited to the particular limitations described. Other implementations may be possible.

We claim:

1. An implantable epidermal paper-based electronic device, consisting of:
   a hydrophilic paper substrate with a first hydrophilic side, wherein the first hydrophilic side is coated with silver nano-flakes (AgNFs), which act as an electrically conductive layer, and a second omniphobic side;
   wherein the hydrophilic paper substrate coated with AgNFs is laser cut into a serpentine pattern to provide stretchability, wherein:
   the device is encapsulated in a biocompatible matrix to implant it in a body.

2. The device of claim 1, wherein the electrically conductive layer further comprises an array of temperature sensors, is configured to be implanted in the body of a subject, and can be used to provide thermal stimulation on underlying tissue of the subject.

3. A method of preparing an implantable epidermal paper-based electronic device, wherein the method comprises:
   providing a sheet of hydrophilic paper substrate with a first and a second side;
   treating the second side of the hydrophilic paper substrate with a silanizing material to make the second side omniphobic;

providing an electrically conductive layer by applying silver nano-flakes on the first side of the hydrophilic paper substrate;

fabricating the device to provide a highly stretchable form; and encapsulating the fabricated device in a biocompatible matrix prior to implanting the device in a body.

4. An implantable epidermal paper-based electronic device consisting of:

an omniphobic paper substrate prepared from a hydrophilic paper substrate by rendering it omniphobic; and a copper film, alone or in further combination with Ag/AgCl attached to a first side of the omniphobic paper substrate to act as an electrically conductive layer;

wherein the omniphobic paper substrate with the electrically conductive layer is laser cut into a serpentine pattern to provide stretchability, wherein:

the device is encapsulated in a biocompatible matrix to implant it in a body.

* * * * *